United States Patent [19]

Schwender et al.

[11] 4,179,509
[45] Dec. 18, 1979

[54] (SUBSTITUTED 2-CARBOXYANILINO)NICOTINIC ACIDS AS INHIBITORS OF ALLERGIC REACTIONS

[75] Inventors: Charles F. Schwender, Dexter, Mich.; Brooks R. Sunday, Hackettstown, N.J.

[73] Assignee: Warner-Lambert Company, Morris Plains, N.J.

[21] Appl. No.: 943,504

[22] Filed: Sep. 18, 1978

[51] Int. Cl.² .................. A61K 31/455; C07D 213/80
[52] U.S. Cl. ...................................... 424/266; 546/310

[58] Field of Search ................. 260/295.5 R; 424/266; 546/310

[56] References Cited

U.S. PATENT DOCUMENTS 3,454,587   7/1969   Littell et al. .................. 260/295.5 R

*Primary Examiner*—Natalie Trousof
*Attorney, Agent, or Firm*—Albert H. Graddis

[57] ABSTRACT

The present invention relates to (substituted 2-carboxyanilino) nicotinic acids which have the capability of inhibiting allergic reactions.

5 Claims, No Drawings

(SUBSTITUTED 2-CARBOXYANILINO)NICOTINIC ACIDS AS INHIBITORS OF ALLERGIC REACTIONS

The present invention encompasses (substituted 2-carboxyanilino) nicotinic acids of the formula:

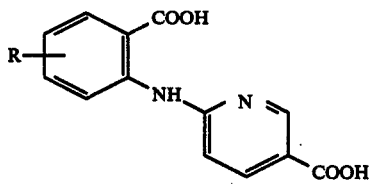

wherein R is selected from the group consisting of hydrogen, alkyl, alkoxy, and halogen, as well as the pharmaceutically acceptable salts thereof.

As used in the above definition for R, alkyl is meant to encompass lower alkyls of 1 to 4 carbon atoms, that is methyl, ethyl, propyl, isopropyl, butyl, and isobutyl radicals; alkoxy is meant to encompass lower alkoxy radicals of 1 to 4 carbon atoms; and halogen is meant to encompass fluorine, chlorine, and bromine radicals.

The pharmaceutically acceptable salts of the compounds of the present invention may be prepared by conventional reactions with equivalent amounts of organic or inorganic solutions. As exemplary, but not limiting, of pharmaceutically acceptable salts are the salts of hydrochloric, sulfuric, acetic, fumeric, malic and citric acids, and appropriate bases such as the hydroxides or bicarbonates of potassium and sodium. The compounds of the present invention which are preferred are those in which R of the generic structure is defined as being hydrogen, methoxy, or methyl.

The compounds of the present invention are synthesized by reacting the appropriately substituted 11-oxo-11-H-pyrido[2,1-b]quinazoline with at least two molecular equivalents of a strong base such as sodium or potassium hydroxide.

It is believed that one of ordinary skill in the art to which this invention pertains can, using the description contained herein, utilize the compounds and methods of the present invention to its fullest extent. The following specific embodiments are, therefore, to be simply construed as merely illustrative and are not meant to limit the scope of the remainder of the specification and claims in any way whatsoever.

EXAMPLE 1

6-(2-Carboxy 4-methylanilino)nicotinic acid

A solution of 10.0 g (39.4 mmol) of 2-methyl-11-oxo-11H-pyrido[2,1-b]quinazoline-8-carboxylic acid and 78.8 ml of 1 N. NaOH in 500 ml of $H_2O$ was heated at reflux for 16 hours. The reaction mixture was evaporated to give a white powder which was triturated with hot EtOH giving the analytical sample upon filtration and drying; yield, 8.25 g (66.5%) mp 348.5° dec.

The compounds of the present invention have been found to reduce allergic responses to antigen challenge by inhibiting antibody-antigen reactions in mammals when tested in accordance with the procedure of Herzig (Immuno-Pharmacology, John Wiley & Son, New York, (1975)). The passive cutaneous anaphylaxis procedure also showed the compounds of the present invention to inhibit the allergic responses in pre-sensitized mammals. This procedure is discussed in detail in U.S. Pat. Nos. 4,028,383 to Brown and Unangst and U.S. Pat. No. 4,076,720 to Connor, Young, and von Strandtmann.

The compounds of the present invention are useful when administered orally at a dose of 0.1 to 10 mg/kg of body weight. These compounds thus are useful in the management of allergic conditions such as that found in bronchial asthma. The compounds of the present generic invention are orally effective and offer a definite advantage over the commerical product 5,5'-[(2-hydroxy-1,3-propanediyl)-bis-(oxy)]-bis[4-oxo-4H-1-benzopyran-2-carboxylic acid], that is the drug intal.

The following table shows the preferred compounds of the present invention, as well as the pharmaceutical results of the PCA standard test protocol:

| R | mp | PCA % inhibition 2 mg/kg, po |
|---|---|---|
| H | 410° dec | 26% |
| 4-CH3 | 348.5° dec | 82% |
| 4-OCH3 | 357°-368° dec | 64% |

Having thus described our invention and manner and process of making and using it in such full, clear, concise, and exact terms as to enable any person skilled in the art to which it pertains, or to which it is more nearly connected to make and use the same, and having set forth the best mode for carrying out our invention,

We claim:

1. A method of inhibiting an allergic reaction in a mammal which comprises administering a compound of the formula:

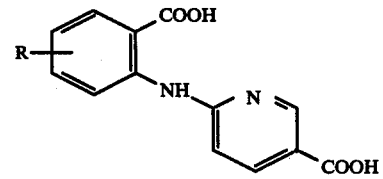

wherein R is selected from the group consisting of hydrogen, or lower alkyl or alkoxy of 1 to 4 carbon atoms and the pharmaceutical salts thereof to a mammal in an amount sufficient to inhibit an allergic reaction.

2. The method according to claim 6 wherein R is selected from the group consisting of hydrogen, methyl, or methoxy.

3. The method according to claim 2 wherein R is hydrogen.

4. The method according to claim 2 wherein R is 4-methyl.

5. The method according to claim 2 wherein R is methoxy.